United States Patent
Zhou

(10) Patent No.: US 9,481,718 B2
(45) Date of Patent: Nov. 1, 2016

(54) EXTRACTING HIRUDIN FROM LEECH IN VIVO

(71) Applicant: North American Hirudin Supplement Products Inc., Seattle, WA (US)

(72) Inventor: Weiguan Zhou, Nanning (CN)

(73) Assignee: North American Hirudin Supplement Products Inc., Seattle, WA (US)

( * ) Notice: Subject to any disclaimer, the term of this patent is extended or adjusted under 35 U.S.C. 154(b) by 0 days.

(21) Appl. No.: 14/691,381

(22) Filed: Apr. 20, 2015

(65) Prior Publication Data

US 2015/0218234 A1  Aug. 6, 2015

(51) Int. Cl.
| | | |
|---|---|---|
| *A61K 38/58* | (2006.01) |
| *A61K 35/62* | (2006.01) |
| *C07K 14/815* | (2006.01) |
| *C07K 14/435* | (2006.01) |
| *A61K 31/7016* | (2006.01) |
| *A61K 31/7004* | (2006.01) |
| *A61K 38/00* | (2006.01) |

(52) U.S. Cl.
CPC ..... *C07K 14/43536* (2013.01); *A61K 31/7004* (2013.01); *A61K 31/7016* (2013.01); *A61K 38/00* (2013.01)

(58) Field of Classification Search
None
See application file for complete search history.

(56) References Cited

FOREIGN PATENT DOCUMENTS

CN  201210493449.7  *  3/2013

OTHER PUBLICATIONS

Website: https://www.nlm.nih.gov/cgi/mesh/2016/MB_cgi, 3 pages, retrieved on May 30, 2016.*

* cited by examiner

Primary Examiner — Satyanarayana R Gudibande
(74) Attorney, Agent, or Firm — Tian IP & Technology, LLC.

(57) ABSTRACT

Described herein relates to methods and compositions for extracting hirudin from a plurality of leeches in vivo. The method may include contacting leeches with inducing membranes containing an inducing agent for a first predetermined time period. The inducing membranes may be removed from the leeches, and the leeches may be contacted with a regurgitation agent for a second predetermined time period in a container such that the leeches are induced to regurgitate regurgitation contents. The regurgitation contents may be collected and purified to obtain the hirudin.

1 Claim, 1 Drawing Sheet

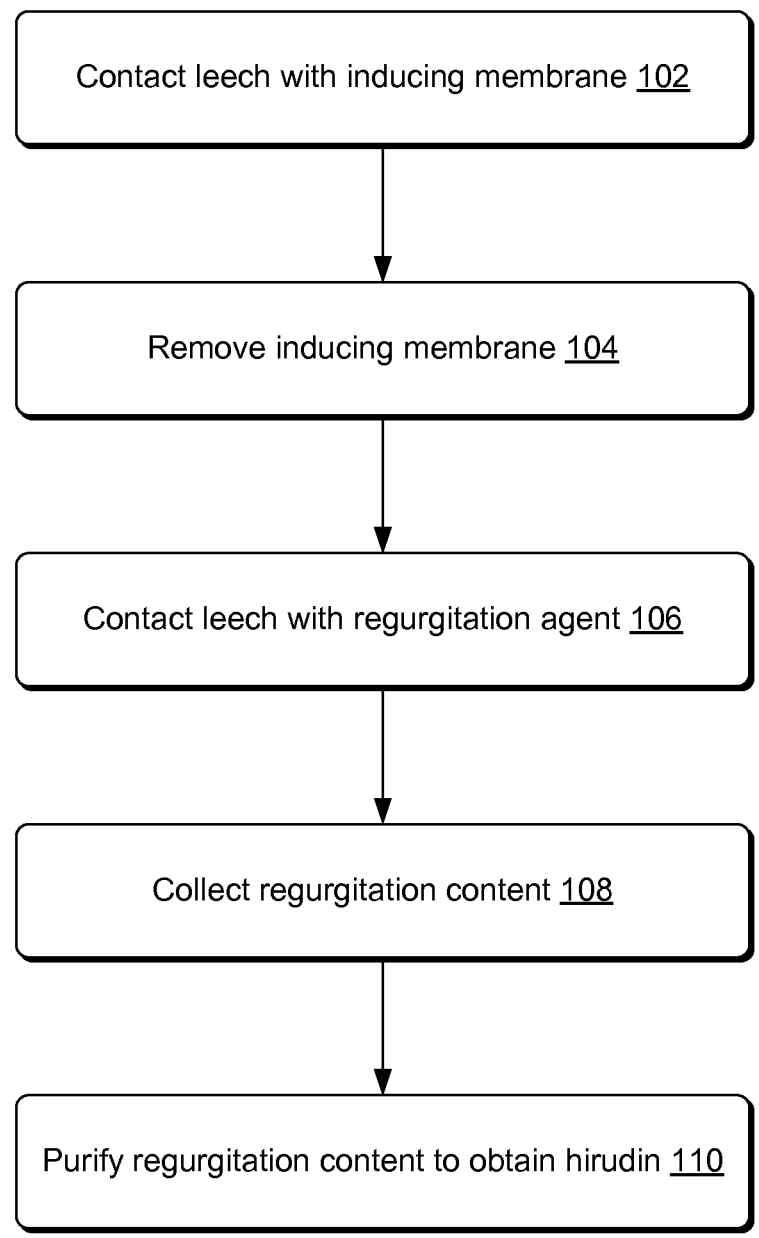

EXTRACTING HIRUDIN FROM LEECH IN VIVO

TECHNICAL FIELD

This disclosure relates to extracting animal content. More specifically, the disclosure relates to extracting hirudin from leeches in vivo.

BACKGROUND

Leeches are segmented worms that belong to the phylum Annelida and comprise the subclass *Hirudinea*. Leeches can be divided into two categories: non-blood-sucking leeches and blood-sucking leeches. Non-blood-sucking leeches are mainly snails and other mollusks that do not suck blood. Blood-sucking leeches living in the rice fields, ditches, rivers, ponds and lakes, and these leeches suck blood of vertebrates including human beings. To suck blood, leeches secrete hirudin, which is a traditional medicine for improving blood circulation.

Hirudin may be extract from medicinal leeches. Under conventional techniques, heads of leeches may be removed, crushed, and then homogenized to obtain a homogenized mixture. The homogenized mixture may be added various chemicals such as acetone mixture or saline solution. The new mixture may be then added additional chemicals to further extract hirudin. Because these techniques involve various chemicals, there is a safety concerns with respect to conditions that some of the harmful chemicals may not be able to be removed from the refined hirudin. Recently, a manual squeezing approach may be used to extract hirudin from leeches. While safer than chemical approaches, the approach not only generates less amount of hirudin but also causes damages on the leeches. These leeches may die and/or generate less amount of hirudin for the next hirudin extraction.

SUMMARY

Implementations of the present disclosure relate to methods for extracting hirudin from a leech in vivo. The method may include contacting leeches with inducing membranes containing an inducing agent for a first predetermined time period. In these instances, the inducing agent may include an aqueous solution containing from about 0.5% to about 3% w/v glycine, from about 0.5% to about 3% alanine, from about 0.5 to about 3% w/v guanylate, from about 0.5 to about 3% w/v uridine monophosphate, from about 1% to 5% w/v trehalose, and from about 1 to 8% w/v glucose. The inducing membranes may be made from at least one of large intestine, small intestine, or casings. The leeches may include a *hirudo* leech or a *manillensis* leech, or a combination thereof, and the leeches may have been cultured for at least 10 days without feeding leech food before the contacting leeches with the inducing membranes.

The method may further include removing the inducing membranes from the leeches and contacting the leeches with a regurgitation agent for a second predetermined time period in a container such that the leeches are induced to regurgitate regurgitation contents at a room temperature. In some implementations, the regurgitation agent may contain 50% ethanol, the regurgitation contents containing unrefined hirudin.

The method may further include collecting the regurgitation contents, purifying the regurgitation contents to obtain refined hirudin, and culturing the leeches without feeding food to the leeches for a third predetermined time period after the collecting the regurgitation contents.

Implementations of the present disclosure relate to methods for extracting hirudin from a leech in vivo. The method may include contacting leeches with inducing membranes containing an inducing agent for a first predetermined time period, removing the inducing membranes from the leeches, contacting the leeches with a regurgitation agent for a second predetermined time period in a container such that the leeches are induced to regurgitate regurgitation contents, collecting the regurgitation contents, and purifying the regurgitation contents to obtain the hirudin.

In some implementations, the leeches may have been cultured without feeding food to the leeches for a third predetermined time period after the collecting the regurgitation contents.

In some implementations, wherein the leeches have not been fed with leech food for at least 10 days before the contacting the leeches with the inducing membranes.

In some implementations, wherein the inducing agent contains an aqueous solution containing at least one of from about 0.5% to about 3% w/v glycine, from about 0.5% to about 3% alanine, from about 0.5 to about 3% w/v guanylate, from about 0.5 to about 3% w/v uridine monophosphate, from about 1% to 5% w/v trehalose, or from about 1 to 8% w/v glucose.

In some implementations, wherein the inducing agent contains an aqueous solution containing from about 0.5% to about 3% w/v glycine, from about 0.5% to about 3% alanine, from about 0.5 to about 3% w/v guanylate, from about 0.5 to about 3% w/v uridine monophosphate, from about 1% to 5% w/v trehalose, and from about 1 to 8% w/v glucose.

In some implementations, wherein the inducing membranes comprise at least one of large intestine, small intestine, or casings.

In some implementations, wherein the regurgitation agent contains 50% ethanol.

In some implementations, wherein the contacting leeches with the inducing membranes, the removing the inducing membrane, the contacting the leeches with the regurgitation agent, and collecting the regurgitation contents are performed at a room temperature.

Implementations of the present disclosure further relate to compositions for facilitating hirudin extraction in vivo. For example, a composition may include an aqueous solution containing from about 0.5% to about 3% w/v glycine, from about 0.5% to about 3% alanine, from about 0.5 to about 3% w/v guanylate, from about 0.5 to about 3% w/v uridine monophosphate, from about 1% to 5% w/v trehalose, and from about 1 to 8% w/v glucose.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The detailed description is described with reference to the accompanying figures.

FIG. 1 is a diagram showing an exemplary process for extracting hirudin from Leeches.

DETAILED DESCRIPTION

Various Implementations of the present disclosure relate to methods and compositions for extracting hirudin from leeches. Unlike conventional techniques, the implementations of the present disclosure may generate hirudin liquid ingredients that are non-toxic, harmless, and non-corrosive. Also, the implementations of the present disclosure allow leeches to be extracted hirudin 3 to 5 times in vivo, therefore increasing efficacy of extractions and reducing the cost.

FIG. 1 is a diagram showing an exemplary process 100 for extracting hirudin from Leeches in vivo. At 102, multiple leeches may be contacted with inducing membranes containing an inducing agent for a first predetermined time period.

Leeches may include any leech having a therapeutic saliva content from which can be extract hirudin. For example, a leech may belong to the family of *hirudinidae*, to the sub-family *hirudinariiae*, or it can belong to a genus selected from the group consisting of *hirudo; hirudinaria; aliolimantis; limantis; asiaticobdella; goddardobdella; limnobdella; macrobdella; oxyptychus; philobdella*. In some implementations, the leech may be selected from a species selected from the group consisting of *hirudo medicinalis; hirudo troctina, hirudo nipponia; hirudo orientalis; hirudo verbana; hirudinaria manillensis; hirudinaria javanica; aliolimantis africana; aliolimantis michaelseni; aliolimantis oligodonta; aliolimantis buntonesis; limantis nilotica; limantis cf. nilotica; limantis paluda; asiaticobdella fenestrata; goddardobdella elegans; limnobdella mexicana; macrobdella decora; macrobdella diploteria; macrobdella diletra; oxyptychus brasiliensis; oxyptychus striatus; philobdella floridana; philobdella gracilis*. In some implementations, the multiple leeches comprising a *hirudo* leech or a *manillensis* leech, or a combination thereof.

The term "hirudin" used herein refers to any forms of hirudin or analogs thereof, naturally isolated from a wide type leech or a genetically modified leech, as long as the desired biological activity is retained. Hirudin is a naturally occurring peptide in the salivary glands of leeches (such as Japanese *hirudo* Leeches, *manillensis* leeches) that has a blood anticoagulant property. Full length of natural hirudin is made up of 65 amino acids, and natural hirudin contains a mixture of various forms (e.g., isoforms) of hirudin. In some implementations, a leech may be fed with an amount of an inducing agent and then contacted with an amount of a regurgitation agent to obtain unrefined hirudin, which contains the inducing agent and other salivary contents (salivary spits). The unrefined hirudin may be refined to obtain refined hirudin by removing the inducing agent.

The term "agent" as used herein means any compound or substance such as, but not limited to, a small molecule, nucleic acid, polypeptide, peptide, drug, ion, etc. An "agent" may be any chemical, entity or moiety, including without limitation synthetic and naturally-occurring proteinaceous and non-proteinaceous entities. In certain implementations, the agent is a compound that may be known to have a desired activity and/or property, or may be selected from a library of diverse compounds. For example, an inducing agent may include one or more compounds and/or substances to facilitate a regurgitation using the inducing agent and to facilitate recovery of leeches after the regurgitation and/or extraction of hirudin. For example, a regurgitation agent may include one or more compounds and/or substances to inducing a regurgitation of a leech. In some implementations, the regurgitation agent may contain from about 25 to about 50% ethanol.

In some implementations, the inducing agent may include an aqueous solution containing at least one of from about 0.1% to about 10% w/v glycine, from about 0.1% to about 10% alanine, from about 0.1 to about 10% w/v guanylate, from about 0.1 to about 10% w/v uridine monophosphate, from about 0.1% to 15% w/v trehalose, or from about 0.1 to 20% w/v glucose. In certain implementations, the inducing agent may include an aqueous solution containing at least one of from about 0.5% to about 3% w/v glycine, from about 0.5% to about 3% alanine, from about 0.5 to about 3% w/v guanylate, from about 0.5 to about 3% w/v uridine monophosphate, from about 1% to 5% w/v trehalose, or from about 1 to 8% w/v glucose.

The term "inducing membrane" used herein refer to a natural membrane or an artificial membrane used to feed a leech with an inducing agent. For example, the inducing membrane may allow the leech to make an incision and to suck the inducing agent. The inducing membrane may include a piece of animal large intestine, small intestine, animal casings or artificial casings, etc. In some implementations, the inducing membranes may be made from at least one of large intestine, small intestine, or casings.

In some implementations, the leeches may have been cultured for at least 10 days without feeding leech food before the contacting leeches with the inducing membranes. In some instances, the leeches may have not been fed with leech food for at least 15 days. For example, the leeches may have not been fed with leech food for at least 15 to 60 days.

In some implementations, the leeches may have been contacted with the inducing membranes for about 10 min to about 60 min. Weight of the leeches may increase 1-10 times after the contacting.

The inducing membranes may be removed from the leeches at 104. For example, the inducing membranes may be removed from the first container, and the leeches may be placed into the second container.

Then, the leeches may be contacted with a regurgitation agent for a second predetermined time period (e.g., 10 min to 30 min) in a container such that the leeches are induced to regurgitate regurgitation contents at a room temperature at 106. For example, the regurgitation agent may contain 50% ethanol, the regurgitation contents containing unrefined hirudin.

The regurgitation contents may be collected at 108. "Regurgitation" and "secretion" are used interchangeably herein refer to activities that a leech regurgitate or vomit its regurgitation contents out of its body. The regurgitation contents may include stomach contents and/or salivary contents of the leech, which contains hirudin.

In some implementations, the contacting leeches with the inducing membranes, the removing the inducing membrane, the contacting the leeches with the regurgitation agent, and collecting the regurgitation contents may be performed at a room temperature.

The regurgitation contents may be purified to obtain refined hirudin at 110. The term "extract" used herein refer to a powder form of the compounds of interest, a liquid form of the compounds of interest, or any one or any combination of the compounds of interest in powder or liquid form. In some implementations, the term "extract" may be used to refer to the compounds of interest before, during, or after their removal from the leech.

It should be appreciated that leech extract may be isolated or purified. In some implementations, the terms "isolated" and "purified" may be used interchangeably. In some implementations, the term "isolated" may be used to refer to an extract removed from the natural chemical environment of the leech such that the extract is not in the form in which it exists in nature. It should be appreciated that the term "purified" may be used to refer to an extract from a leech, for example, such that the compounds of interest are isolated from the remainder of the leech in a form that may be administered to a subject, such as a soluble form, or a form that may go into aqueous solution. As such, one of skill will appreciate that the compounds of interest may sometimes be accompanied by other components that are carried along with the extract. For example, such other components may include any one or any combination of proteins found to be active in the leech. In some implementations, the term "purified" may be used to refer to an extract include any one or any combination of the compounds of interest. In some implementations, the extract includes an inducing agent and/or a regurgitation agent.

The leeches may be then farmed and/or cultured without feeding food to the leeches for a third predetermined time period after the collecting the regurgitation contents.

Implementations of the present disclosure also relate to compositions for facilitating hirudin extraction in vivo. A composition may include an aqueous solution containing from about 0.5% to about 3% w/v glycine, from about 0.5% to about 3% alanine, from about 0.5 to about 3% w/v guanylate, from about 0.5 to about 3% w/v uridine monophosphate, from about 1% to 5% w/v trehalose, and from about 1 to 8% w/v glucose.

Trehalose may have a protective effect on leeches and therefore improve disease resistance of the leeches. For example, trehalose may be found at the cell surface and form a unique protective film, effectively protecting the leeches. Meanwhile, trehalose is an immune enhancer or modifier, which may enhance immune functions of the leeches. For example, trehalose may improve the intestinal environment within the leeches' body, and promote beneficial bacteria Lactobacillus population growth to maintain balance and stability of the intestinal microflora flora of the leeches. Therefore, trehalose may prevent and/or treat various viral infections and/or bacterial diseases during and after hirudin extractions.

In vivo metabolism of glucose generates exothermic heat for leeches. A certain amount of glucose in the inducing agent may allow the leeches quickly add energy to restore the physical and energy levels as compared to the leeches without being extracted hirudin.

In some implementations, the regurgitation agent may include 50% ethanol solution, which may induce regurgitations without damaging the skin of leeches. By using the combination of the inducing agent and the regurgitation agent, the leeches may be repeated to extract hirudin 3 to 5 times, and each leech may be extract unrefined hirudin about 5 to 50 ml.

In some implementations, a Markwardt thrombin titration assay may be used to measure contents of the active ingredient: hirudin.

The various implementations described above can be combined to provide further implementations. Aspects of the implementations can be modified, if necessary to employ concepts of the various patents, applications and publications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

EXAMPLES

Example 1

An inducing agent may be provided to facilitate hirudin extraction. The inducing agent contains glycine about 5% (w/v), alanine about 5% (w/v), guanylate about 5% (w/v), uridine monophosphate about 5% (w/v), trehalose about 10% (w/v), glucose about 10% (w/v). After removing contents from a pig duodenum, the pig duodenum was filled with the above prepared inducing agent about 15000 ml. The filled pig duodenum was segmented by every about 50 cm. After filling, the inducing intestine piece was fastened at both ends to make it swell.

1528 gram (g) of *manillensis* leeches were selected and dispersing them into a first container. These leeches have not been feed for at least about 20 days. Then, the inducing intestine pieces were placed in the first container for about 30 minutes (min) such that the leeches contact with the inducing intestine pieces and suck the inducing agent. After feeding, the leeches gain weight up to 8035 g. Therefore, the weight of the contacted leeches are about 5 times of the weight of those without contacting with the inducing agent.

The contacted leeches may be placed into a second container and the second container was then filled with a regurgitation agent about 1931 g to allow the leeches to regurgitate regurgitation contents into the second container. The regurgitation agent contains about 50% ethanol solution.

The leeches were contacted with the ethanol solution for about 10 min. Then, the leeches were removed from the second container, rinsed with water. The leeches were placed into a third container and raised without feeding any food until the next extraction.

After removing the leeches, the second container included about 7177 g solution containing the unrefined hirudin. According, an individual leech was extracted unrefined hirudin about 17 to 50 ml (not including 50% ethanol).

The unrefined hirudin into the second containers was further purified. First, 7177 g solution was filtered using a 100 mesh screening filter. The filtered solution was placed a 60° C. water bath for about 30 minutes, and then cooled to a room temperature. The filtered solution was then filtered again using a 150 mesh screening filter mesh screening filter and centrifuged using about 15,000 rev/min for 15 minutes to obtain filtrate. The filtrate was then pass through an ultrafiltration membrane with a molecular weight 7000 D to obtain a concentrated solution 2882 ml, which contains hirudin about 84 AT-U/ml. Antithrombin activity of the concentrated solution was measured to indicate the amount of hirudin. Medicinal starch 100 g was added to the concentrated solution to obtain a mixture. A freeze-drying operation was performed on the mixture to obtain hirudin powder about 103 g, which contains hirudin about 2340 AT-U/g.

Example 2

An inducing agent may be provided to facilitate hirudin extraction. The inducing agent contains glycine about 3% (w/v), alanine about 3% (w/v), guanylate about 3% (w/v), uridine monophosphate about 3% (w/v), trehalose about 5% (w/v), glucose about 8% (w/v).

After removing contents from a pig intestine, the pig intestine was filled with the above prepared inducing agent about 8000 ml. The filled pig intestine was segmented by every about 20 cm. After filling, the inducing intestine piece was fastened at both ends to make it swell.

786 gram (g) of Japanese *hirudo* Leeches were selected and dispersing them into a first container. These leeches have not been feed for at least 55 days. Then, the inducing intestine pieces were placed in the first container for about 20 minutes (min) such that the leeches contact with the inducing intestine pieces and suck the inducing agent. After feeding, the leeches gain weight up to about 5761 g. Therefore, the weight of the contacted leeches are about 7 times of the weight of those without contacting with the inducing agent.

The contacted leeches may be placed into a second container and the second container was then filled with a regurgitation agent about 1309 g to allow the leeches to regurgitate regurgitation contents into the second container. The regurgitation agent contains about 50% ethanol solution.

The leeches were contacted with the ethanol solution for about 25 min. Then, the leeches were removed from the second container, rinsed with water. The leeches were placed into a third container and raised without feeding any food until the next extraction.

After removing the leeches, the second container included 5556 g solution containing the unrefined hirudin. According, an individual leech was extracted unrefined hirudin about 5 to 22 ml (not including 50% ethanol).

The unrefined hirudin into the second containers was further purified. First, the 5556 g solution was filtered using a 120 mesh screening filter. The filtered solution was placed an about 70° C. water bath for 40 minutes, and then cooled to a room temperature. The filtered solution was then filtered again using a 200 mesh screening filter mesh screening filter and centrifuged using 10,000 rev/min for 20 minutes to obtain filtrate. The filtrate was then pass through an ultrafiltration membrane with a molecular weight 7000 D to obtain a concentrated solution 1964 ml, which contains hirudin about 48 AT-U/ml. Mannitol about 600 g was added to the concentrated solution to obtain a mixture. A freeze-drying operation was performed on the mixture to obtain hirudin powder about 601 g, which contains hirudin about 157 AT-U/g.

Example 3

An inducing agent may be provided to facilitate hirudin extraction. The inducing agent contains glycine about 0.5% (w/v), alanine about 2.5% (w/v), guanylate about 1.5% (w/v), uridine monophosphate about 4% (w/v), trehalose about 5% (w/v), glucose about 6% (w/v).

After removing contents from a casings, the casings was filled with the above prepared inducing agent about 28000 ml. The filled casings was segmented by every about 100 cm. After filling, the inducing intestine piece was fastened at both ends to make it swell.

2486 gram (g) of Japanese *hirudo* Leeches were selected and dispersing them into a first container. These leeches have not been feed for at least about 60 days. Then, the inducing intestine pieces were placed in the first container for about 60 minutes (min) such that the leeches contact with the inducing intestine pieces and suck the inducing agent. After feeding, the leeches gain weight up to about 20234 g. Therefore, the weight of the contacted leeches are about 8 times of the weight of those without contacting with the inducing agent.

The contacted leeches may be placed into a second container and the second container was then filled with a regurgitation agent 3250 g to allow the leeches to regurgitate regurgitation contents into the second container. The regurgitation agent contains about 50% ethanol solution.

The leeches were contacted with the ethanol solution for about 10 min. Then, the leeches were removed from the second container, rinsed with water. The leeches were placed into a third container and raised without feeding any food until the next extraction.

After removing the leeches, the second container included about 17567 g solution containing the unrefined hirudin. According, an individual leech was extracted unrefined hirudin about 5 to 25 ml (not including 50% ethanol).

The unrefined hirudin into the second containers was further purified. First, the 17567 g solution was filtered using a 150 mesh screening filter. The filtered solution was placed a about 62° C. water bath for 38 minutes, and then cooled to a room temperature. The filtered solution was then filtered again using a 180 mesh screening filter mesh screening filter and centrifuged using about 3,000 rev/min for about 30 minutes to obtain filtrate. The filtrate was then pass through an ultrafiltration membrane with a molecular weight 7000 D to obtain a concentrated solution 887 ml, which contains hirudin about 227 AT-U/ml. Soluble starch 250 g was added to the concentrated solution to obtain a mixture. A freeze-drying operation was performed on the mixture to obtain hirudin powder about 243 g, which contains hirudin about 806 AT-U/g.

Example 4

An inducing agent may be provided to facilitate hirudin extraction. The inducing agent contains glycine about 1.6% (w/v), alanine about 2.5% (w/v), guanylate about 1.1% (w/v), uridine monophosphate about 2.1% (w/v), trehalose about 4.2% (w/v), glucose about 6.9% (w/v).

After removing contents from a casings, the casings was filled with the above prepared inducing agent 50000 ml. The filled casings was segmented by every 10 cm. After filling, the inducing intestine piece was fastened at both ends to make it swell.

4659 g of *Manillensis* Leeches were selected and dispersing them into a first container. These leeches have not been feed for at least about 25 days. Then, the inducing intestine pieces were placed in the first container for about 57 minutes (min) such that the leeches contact with the inducing intestine pieces and suck the inducing agent. After feeding, the leeches gain weight up to about 14995 g. Therefore, the weight of the contacted leeches are about 3 times of the weight of those without contacting with the inducing agent.

The contacted leeches may be placed into a second container and the second container was then filled with a regurgitation agent about 2500 g to allow the leeches to regurgitate regurgitation contents into the second container. The regurgitation agent contains about 50% ethanol solution.

The leeches were contacted with the ethanol solution for about 24 min. Then, the leeches were removed from the second container, rinsed with water. The leeches were placed into a third container and raised without feeding any food until the next extraction.

After removing the leeches, the second container included about 12245 g solution containing the unrefined hirudin. According, an individual leech was extracted unrefined hirudin about 10 to 34 ml (not including 50% ethanol).

The unrefined hirudin into the second containers was further purified. First, the 12245 g solution was filtered using a 120 mesh screening filter. The filtered solution was placed an about 67° C. water bath for about 55 minutes, and then cooled to a room temperature. The filtered solution was then filtered again using a 150 mesh screening filter mesh screening filter and centrifuged using about 8,000 rev/min for about 24 minutes to obtain filtrate. The filtrate was then pass through an ultrafiltration membrane with a molecular weight 7000 D to obtain a concentrated solution 3568 ml, which contains hirudin about 85 AT-U/ml. Maltodextrin about 1000 g was added to the concentrated solution to obtain a mixture. A spray drying operation was performed on the mixture to obtain hirudin powder about 926 g, which contains hirudin about 278 AT-U/g.

Example 5

An inducing agent may be provided to facilitate hirudin extraction. The inducing agent contains glycine about 1.3% (w/v), alanine about 2.5% (w/v), guanylate about 2.9% (w/v), uridine monophosphate about 1.7% (w/v), trehalose about 4.2% (w/v), glucose about 6.3% (w/v).

After removing contents from a pig duodenum, the pig duodenum was filled with the above prepared inducing agent about 12000 ml. The filled pig duodenum was segmented by every about 35 cm. After filling, the inducing intestine piece was fastened at both ends to make it swell.

1046 g of *Manillensis* Leeches were selected and dispersing them into a first container. These leeches have not been feed for at least about 60 days. Then, the inducing intestine pieces were placed in the first container for about 55 minutes (min) such that the leeches contact with the inducing intestine pieces and suck the inducing agent. After feeding, the leeches gain weight up to about 4533 g. Therefore, the weight of the contacted leeches are about 4 times of the weight of those without contacting with the inducing agent.

The contacted leeches may be placed into a second container and the second container was then filled with a regurgitation agent about 700 g to allow the leeches to regurgitate regurgitation contents into the second container. The regurgitation agent contains about 50% ethanol solution.

The leeches were contacted with the ethanol solution for about 10 min. Then, the leeches were removed from the second container, rinsed with water. The leeches were placed into a third container and raised without feeding any food until the next extraction.

After removing the leeches, the second container included 3665 g solution containing the unrefined hirudin. According, an individual leech was extracted unrefined hirudin about 12 to 41 ml (not including 50% ethanol).

The unrefined hirudin into the second containers was further purified. First, the 3665 g solution was filtered using a 150 mesh screening filter. The filtered solution was placed an about 63° C. water bath for about 55 minutes, and then cooled to a room temperature. The filtered solution was then filtered again using a 100 mesh screening filter mesh screening filter and centrifuged using about 5,000 rev/min for about 30 minutes to obtain filtrate. The filtrate was then pass through an ultrafiltration membrane with a molecular weight 7000 D to obtain a concentrated solution 1156 ml, which contains hirudin about 102 AT-U/ml. Mannitol about 300 g was added to the concentrated solution to obtain a mixture. A spray drying operation was performed on the mixture to obtain hirudin powder about 287 g, which contains hirudin about 411 AT-U/g.

What is claimed is:

1. A method for extracting hirudin from leeches in vivo, the method comprising following steps in a chronological order:
   (1) contacting the leeches with inducing membranes containing an inducing agent for from about 10 minutes to 60 minutes, the inducing agent comprising an aqueous solution containing about 3% w/v glycine, about 3% alanine, about 3% w/v uridine monophosphate, about 5% w/v trehalose, and about 8% w/v glucose, the inducing membranes made from at least one of large intestine, small intestine, or casings, the leeches comprising a *hirudo* leech or a *manillensis* leech, or a combination thereof, the leeches having been cultured for at least 10 days without feeding leech food before the contacting leeches with the inducing membranes;
   (2) removing the inducing membranes from the leeches;
   (3) contacting the leeches with a regurgitation agent for from about 10 minutes to 30 minutes in a container such that the leeches are induced to regurgitate regurgitation contents at a room temperature, the regurgitation agent containing 50% ethanol, the regurgitation contents containing unrefined hirudin;
   (4) collecting the regurgitation contents containing unrefined hirudin;
   (5) purifying the regurgitation contents to obtain refined hirudin; and
   (6) culturing the leeches without feeding food to the leeches for a predetermined time period after the collecting the regurgitation contents.

* * * * *